United States Patent [19]
Gernhart et al.

[11] Patent Number: 4,962,669
[45] Date of Patent: Oct. 16, 1990

[54] METHOD AND APPARATUS FOR MEASURING DEFORMATIONS OF TEST SAMPLES IN A TESTING MACHINE

[75] Inventors: Peter Gernhart, Klingenberg; Gerhart Hintz, Rossdorf; Guenter Keller, Modautal; Werner Treusch, Fraenkisch Crumbach; Karl Zoeller, Alsbach-Haehnlein, all of Fed. Rep. of Germany

[73] Assignee: Carl Schenck AG, Darmstadt, Fed. Rep. of Germany

[21] Appl. No.: 418,400

[22] Filed: Oct. 6, 1989

Related U.S. Application Data

[63] Continuation-in-part of Ser. No. 207,754, Jun. 16, 1988, abandoned.

[30] Foreign Application Priority Data

Jun. 19, 1987 [DE] Fed. Rep. of Germany ....... 3720248

[51] Int. Cl.$^5$ .............................................. G01L 1/24
[52] U.S. Cl. .................................................... 73/800
[58] Field of Search ...................... 73/800; 356/32, 33, 356/35.5, 372, 375, 383

[56] References Cited

U.S. PATENT DOCUMENTS

| | | |
|---|---|---|
| 2,629,256 | 2/1953 | Rank . |
| 3,592,545 | 7/1971 | Pane et al. . |
| 4,031,746 | 6/1977 | Furuta et al. . |
| 4,605,857 | 8/1986 | Ninomiya et al. . |
| 4,690,001 | 9/1987 | Harvey et al. .......................... 73/800 |

FOREIGN PATENT DOCUMENTS

| | | |
|---|---|---|
| 0023643 | 2/1981 | European Pat. Off. . |
| 0194354 | 12/1985 | European Pat. Off. . |
| 0255552 | 2/1988 | European Pat. Off. . |
| 0534151 | 9/1931 | Fed. Rep. of Germany ........ 73/800 |
| 880510 | 5/1953 | Fed. Rep. of Germany . |
| 1278758 | 9/1968 | Fed. Rep. of Germany . |
| 2155233 | 5/1973 | Fed. Rep. of Germany . |
| 1773642 | 1/1974 | Fed. Rep. of Germany . |
| 2330162 | 12/1974 | Fed. Rep. of Germany . |
| 2602583 | 7/1976 | Fed. Rep. of Germany . |
| 2631663 | 1/1978 | Fed. Rep. of Germany . |
| 3151542 | 7/1983 | Fed. Rep. of Germany . |
| 3209582 | 9/1983 | Fed. Rep. of Germany . |
| 3346429 | 7/1985 | Fed. Rep. of Germany . |
| 3422988 | 1/1986 | Fed. Rep. of Germany . |
| 3638338 | 11/1986 | Fed. Rep. of Germany . |
| 2567264 | 1/1986 | France . |
| 0238852 | 8/1969 | U.S.S.R. ................................. 356/32 |
| 895600 | 5/1962 | United Kingdom . |
| 1294234 | 10/1972 | United Kingdom . |

OTHER PUBLICATIONS

"Experimentelle Technik Der Physik", 1960, No. 3, pp. 126–132, by Herrendoerfer et al.
VDI Berichte No. 631, 1987, "Strain Measurement of Multilayer Components By The Diffraction Principle", by H. Goetting et al.
Journal of Scientific Instruments (Journal of Physics E) 1969 Series 2, vol. 2; pp. 375–377, Article Entitled: "The Application of a Light-Sensitive Potentiometer in the Measurement of the Mechanical Properties of Single Fibers".

*Primary Examiner*—Robert Raevis
*Attorney, Agent, or Firm*—W. G. Fasse; D. H. Kane, Jr.

[57] ABSTRACT

A method for measuring deformations of test samples in testing machines is carried out in a device including a light source, a detector, and signal processing circuitry. The deformations are sensed in that a light beam (2) from the light source (1) is reflected by at least one mirror (6, 6', 6a, 6b, 11a, 11b) arranged at an appropriate location, for example, directly on the test sample (4) so that test sample movements are imparted directly or indirectly to the reflecting mirror or mirrors, whereby the reflected light beam impinges upon a position detector (7) and the position of the impingement or rather its movement is determined and evaluated in an electronic evaluating circuit (8). This movement is a direct measure of the deformation. The device includes components for carrying out these method steps, whereby it is possible to measure static and/or dynamic deformations caused by tensile and compressive forces, as well as deformations resulting from twisting torques and bending moments. Furthermore, it is possible to simultaneously measure several different deformation types.

9 Claims, 3 Drawing Sheets

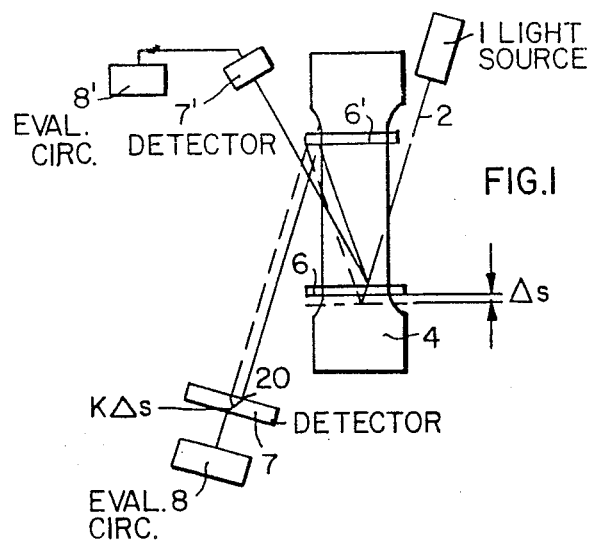
FIG.1
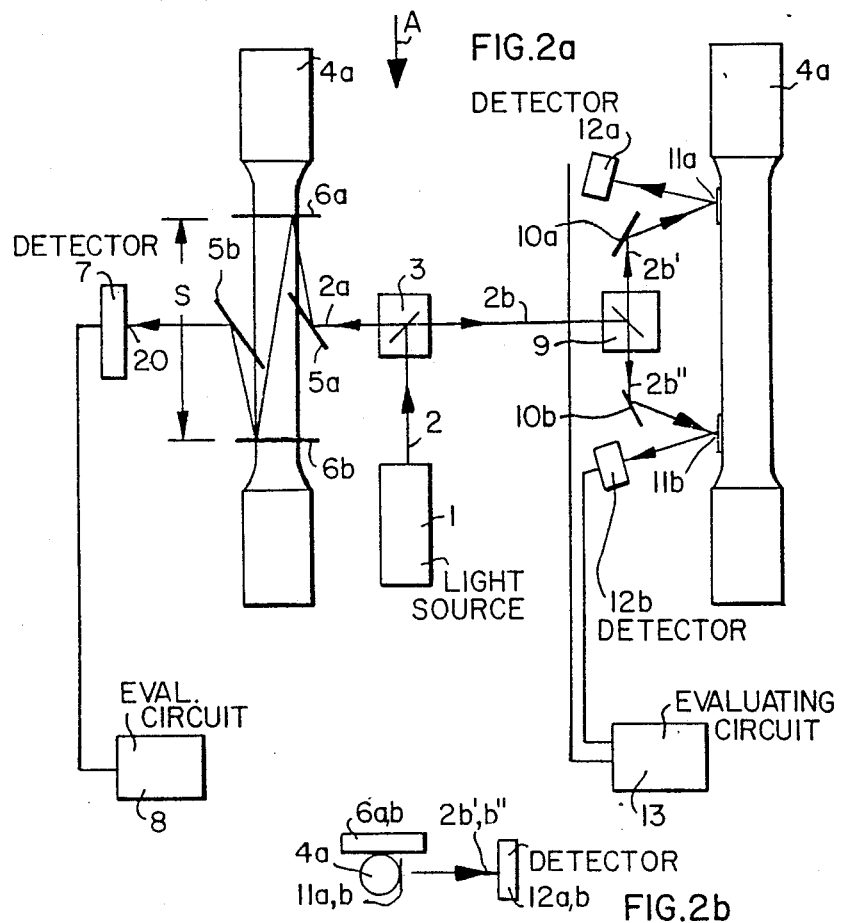
FIG.2a
FIG.2b

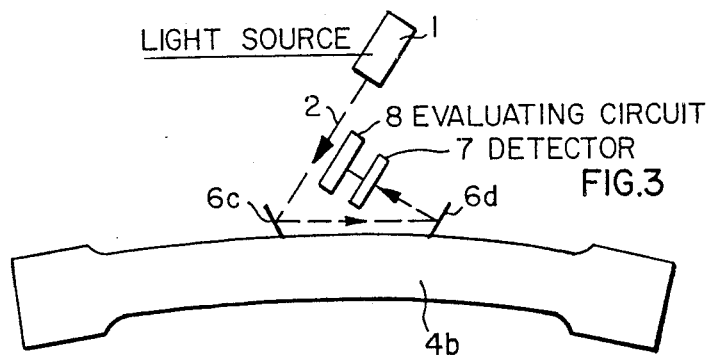
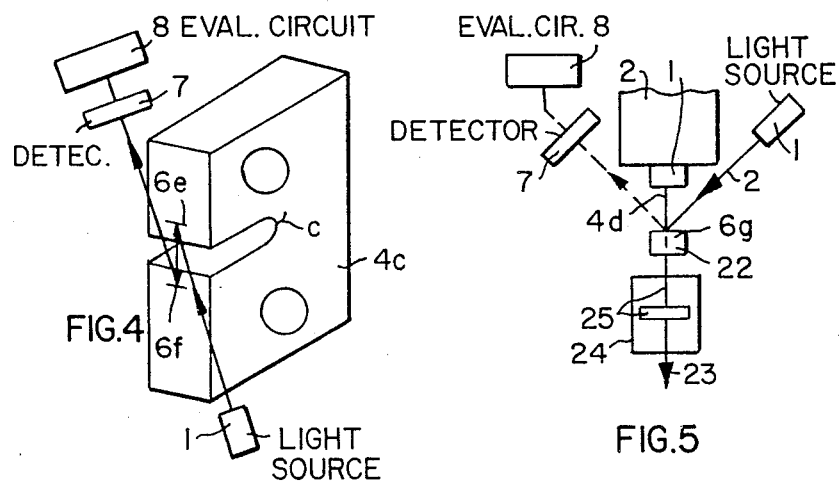
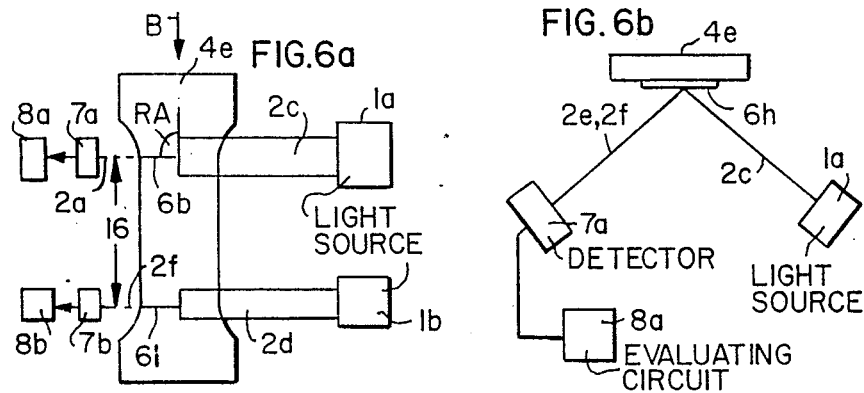

METHOD AND APPARATUS FOR MEASURING DEFORMATIONS OF TEST SAMPLES IN A TESTING MACHINE

CROSS-REFERENCE TO RELATED APPLICATIONS

The present application is a continuation-in-part application of U.S. Ser. No. 07/207,754, filed on June 16, 1988, (now abandoned) and entitled: METHOD AND APPARATUS FOR MEASURING DEFORMATIONS OF TEST SAMPLES IN A TESTING MACHINE. The present application also relates to U.S. Ser. No. 207,729, filed on June 16, 1988; now U.S. Pat. No. 4,836,031 and to U.S. Ser. No. 207,758, also filed on June 16, 1988; now U.S. Pat. No. 4,821,579.

FIELD OF THE INVENTION

The invention relates to a method for measuring deformations of test samples in testing machines by using a light source and signal processing circuitry. The invention further relates to an apparatus for carrying out the present method.

1. Background Information

German Patent Publication No. 3,422,988 (Eisenreich et al.), published on Jan. 2, 1986, discloses a conventional method for a contactless measurement of cross-contractions of an elongated structural component that is subjected to longitudinal tension stress. The sample is illuminated in the crosswise direction by a light beam having a defined cross-sectional area. The light proportion appearing behind the sample. As the sample contracts, more light will be detected behind the sample than when the sample has its original width. The increase in the light quantity measured is a precise measure for the contraction or rather the extent of the contraction. The shutter through which the light is passed to illuminate the sample, is not attached to the sample.

2. Objects of the Invention

In view of the foregoing it is the aim of the invention to achieve the following objects singly or in combination:

- to accurately measure deformations of test samples in the micron range in testing machines, by means of the methods and apparatus described herein;
- to accurately measure static and/or dynamic deformations caused on test samples by tensile forces, compressive forces, torque moments and/or bending moments;
- to accurately measure so-called crack widening deformations;
- to achieve the simultaneous measurement of axial deformations and twisting deformations under static or dynamic tensile, compressive, and/or torsional loading in testing machines;
- to achieve deformation measurements under cyclic loading conditions;
- to achieve path and velocity measurements in extremely accelerated test samples, for example, in rapid tensile rupture test machines;
- to avoid the effect of movement or vibration of the entire testing machine on the resultant accurate measurements;
- to provide for the automatic compensation of geometrical misalignments of components of the apparatus; and
- to provide a method and apparatus that is easily adapted to different specific test samples and different testing requirements.

SUMMARY OF THE INVENTION

The above objects have been achieved by a method for measuring deformations of test samples in testing machines according to the invention, wherein a light beam from a light source is directed onto at least one mirror or reflector arranged at an appropriate location on the test sample, whereby the light beam is reflected toward a position sensor or detector. An electronic evaluating circuit evaluates the output signal of the position detector for determining a movement of the light beam impinging location on the position detector, whereby a deformation corresponding to said movement is measured. The light beam may be additionally guided or directed by means of at least one beam splitter and at least one redirecting mirror. By appropriately arranging light directing elements on the test sample or on the testing machine, the present method may be used for measuring deformations including elongation, compression, torsion, bending, crack opening, and rapid motion characteristics of test samples or any simultaneous combination of several of these deformation types.

An arrangement for carrying out the method according to the invention includes a light source emitting a point cross-section or line cross-section light beam, at least one mirror or reflector arranged at an appropriate location on the test sample, a position sensor detector, and electronic evaluating circuitry connected to the position detector for evaluating the output signal of the position detector. Further light directing elements such as beam splitters and/or redirecting mirrors may additionally be provided. The position detector or sensor as well as the evaluating circuitry may operate in an analog or digital manner.

BRIEF DESCRIPTION OF THE DRAWINGS

In order that the invention may be clearly understood, it will now be described, by way of example, with reference to the accompanying drawings, wherein:

FIG. 1 is a schematic front view of a general arrangement for measuring, according to the invention, deformations of a test sample;

FIG. 2a is a front view of an arrangement for simultaneously measuring axial and torsional deformations of a single test sample which is shown twice for convenience of illustration;

FIG. 2b is a view of the arrangement of FIG. 2a, approximately in the direction of the arrow A in FIG. 2a, whereby it becomes clear that all mirrors or reflecting surfaces are attached to one test sample;

FIG. 3 is a front schematic view of an arrangement for measuring bending deformations of a test sample;

FIG. 4 is a perspective view of an arrangement for measuring the widening of a crack;

FIG. 5 is a schematic front view of an arrangement for measuring rapid movements or accelerations of test samples;

FIG. 6a is a front view of an arrangement using a light source emitting one or two light beams having a line cross-section;

FIG. 6b is a top view onto the arrangement of FIG. 6a in the direction of arrow B in FIG. 6a.

Figure 6C:
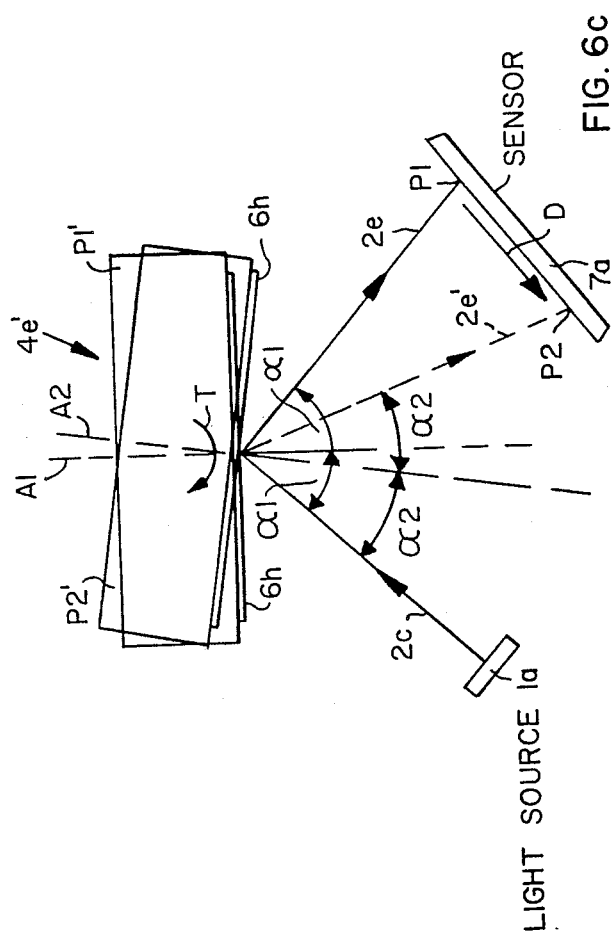
FIG. 6c is a schematic illustration of a view similar to FIG. 6b for explaining the ability of the embodiment of FIGS. 6a and 6b to measure torque caused distortions.

DETAILED DESCRIPTION OF PREFERRED EXAMPLE EMBODIMENTS AND OF THE BEST MODE OF THE INVENTION

As shown in FIG. 1, a light source 1 emitting a collimated, point cross-section light beam 2 directs the light beam onto a first mirror 6 reflecting the light beam onto a second mirror 6'. The mirrors 6 and 6' are attached to a test sample 4 with the respective mirror surface planes extending perpendicularly relative to the lengthwise axis of the test sample 4. The test sample 4 may be a standard round section or flat section test sample. The light beam 2 is finally reflected by the second mirror 6' and directed onto a position detector 7. The detector 7 is, for example, a typical known optical electronic position detector such as S 1352 made by Hamamatsu Photonics. The detector 7 outputs a signal which is dependent upon the position of the light point 20 at which the light beam 2 impinges upon the sensor surface of the detector 7, thereby forming an impingement location. The output signal of the detector 7 is evaluated in an electronic evaluating circuit 8 in order to measure with high accuracy any movement of the impingement location formed by the light point 20. Thus, any movements of the mirrors 6 or 6' caused by a deformation or deformations of the test sample 4 may be accurately determined or measured. Alternatively, a position detector 7' may be arranged to receive the light beam 2 directly reflected by the mirror 6, thereby avoiding the use of a second mirror 6'. In either case, any variation in length $\Delta s$ of the test sample 4 results in a deviation of the reflected path of the light beam 2 which results in a deviation or movement $K \times \Delta s$ of the impingement location of the point 20 of the light beam 2 on the detector 7 or 7'. The movement of the impingement location of the point 20 of the light is evaluated in the evaluating circuit 8 to determine and, for example, display or print out length variation $\Delta s$ of the test sample 4. The position detector 7 may be a one-axis or a two-axis detector. That is to say, it may detect movement of a light point on a one-axis line or on a two-axis plane. In this manner, deformations or distances in the micron range can be measured.

Incidentally, the electronic evaluating circuit is a circuit of the type MV 319 manufactured by Carl Schenck AG or the circuit of FIG. 7 of Dr. Seitner/Hamamatsu pamphlet 26.S . . . 0883. The arrangement shown in FIGS. 2a and 2b can be used for a combined simultaneous measurement of axial and torsional deformations of a single test sample 4a shown twice in FIG. 2a to simplify to illustration of the light beam paths. As shown especially in FIG. 2a, a light source 1, especially a laser light source 1, emits a collimated point cross-section light beam 2 which is split into two partial beams 2a and 2b by means of an optical beam splitter 3. The partial beam 2a is used for measuring the axial deformation or elongation of the test sample 4a as a result of a testing force applied to the test sample 4a by conventional means not shown. In order to achieve this, the beam 2a may be directed as described for the arrangement of FIG. 1 above or preferably, may be reflected by an adjustable redirecting mirror 5a to a mirror 6a which reflects the light beam to a second mirror 6b. The mirror 6b reflects the light to a second adjustable redirecting mirror 5b which in turn directs the light to the position detector 7. The mirrors 6a and 6b are attached either rigidly or spring elastically by means of spring clips to the test sample 4a. The spacing s between the mirrors 6a and 6b corresponds to the measurement baseline of a typical strain gage. The relative change $\Delta s$ in the spacing between the mirrors 6a and 6b corresponds to the lengthwise elongation or deformation of the test sample 4a in the example shown.

The change $\Delta s$ in the spacing between the mirrors 6a and 6b causes the beam 2a to impinge on the redirecting mirror 5b at another impingement location, whereby the location of the point 20 of impingement of the beam 2a onto the position detector 7 also changes. The detector 7 is the same opto-electronic position detector as mentioned above, for generating a position proportional output current representing the movement of the light beam 2a. The output current of the detector 7 is converted in the electronic evaluating circuit 8 into position proportional voltage signals which are displayed as an indication of the change in the spacing between the mirrors 6a and 6b. Such change corresponds directly to the elongation deformation $\Delta s$ of the test sample 4a. Either analog or digital detectors and evaluating circuitry may be used in the arrangement according to the invention.

Any movements of the mirrors 6a and 6b caused by an elastic deformation movement of the testing machine itself, are compensated by the total arrangement of the mirror system, because both mirrors 6a and 6b follow any such movement of the testing machine in unison. Hence, only a change in the relative positions of the two mirrors 6a and 6b, namely a deformation $\Delta s$ of the test sample 4a between the two mirrors, can result in a signal indicating a change in the impingement location and hence a deformation of the test sample.

Now referring to the right portion of FIG. 2a, the partial light beam 2b exiting from the beam splitter 3 is used for measuring the torsional strain or twisting of the test sample 4a. Here again, the means for applying a testing torque to the test sample 4a are conventional and not shown. The partial light beam 2b is further split into partial beams 2b' and 2b" by means of a beam splitter 9. The partial light beams 2b' and 2b" are reflected respectively by adjustable redirecting mirrors 10a and 10b, toward mirrors 11a and 11b attached to the test sample 4a. The partial beams are reflected by the mirrors 11a and 11b onto position detectors 12a and 12b. A rotational movement of the mirrors 11a or 11b causes a movement of the impingement location of the light points on the detectors 12a or 12b, which generate a corresponding photoelectric current. Thus, the respective output signals of the detectors 12a and 12b represent the rotational movement of the mirrors 11a and 11b, and hence the torque applied to the test sample. These signals are converted into corresponding, proportional electric voltages in the electronic evaluating circuit 13 of the same type as disclosed above. By subtracting the electrical output signal of one position detector from that of the other position detector, the angular value of the torsional deformation of the test sample is determined by the electronic circuitry. Geometrical errors of the mirror system, for example, errors in the initial alignment, are automatically compensated, in that the initial alignment of the mirror system, before any deformation of the test sample takes place, is taken as the initial null point.

FIG. 2b shows a view approximately in the direction of the arrow A in FIG. 2a to clarify the arrangement on a single test sample 4a of the mirrors 6a and 6b for measuring an axial deformation, and mirrors 11a and 11b for measuring a rotational or torque deformation.

In the described arrangement, the spacing between the mirrors 6a and 6b, and the angle of incidence of the light beam, as well as other arrangement parameters can easily be adapted to the respective testing conditions such as test sample size and shape. In this manner, nearly any desired measurement basis can be provided and any practically relevant distance or displacement measurements can be achieved.

FIG. 3 shows an arrangement according to the invention for determining or measuring bending deformations of a test sample 4b. A light source 1 emits a light beam 2 which is reflected in sequence by mirrors 6c and 6d to impinge upon the position detector 7 connected with its output to an electronic evaluating circuit 8 for evaluating the output signal of the detector 7 in order to determine a measure of the bending deformation of the test sample 4b. If the position detector 7 is a two-axis detector, this arrangement may simultaneously be used to determine lengthwise strain, or deformation in the axial direction of the test sample 4b as well as bending and torque deformations as described. The separate components of the arrangement of FIG. 3 are similar to the components described above and hence need not be described in further detail here.

FIG. 4 shows an arrangement for determining the growth or widening of a crack C in a compact tension or CT test sample 4c. A light source 1, mirrors 6e and 6f, a position detector 7, and an evaluating circuit 8 are arranged as shown and function in a manner similar to the components described above.

FIG. 5 shows an arrangement for measuring deformations of a test sample 4d and/or the deformation velocity in a rapid tensile rupture testing machine having a first clamping head 21 and a second clamping head 22 for clamping a test sample 4d. For the test, for example, the head 22 is rapidly moved away from the head 21 as indicated by the arrow 23 by impinging of an accelerated element 24 on a cam device 25. In such machines, performing the measurements of interest directly at the test sample becomes extremely difficult and costly. By arranging a mirror or reflecting surface 6g on the clamping head 22, in this manner, usable measurement results can be achieved at a minimal cost and effort. A light beam 2 emitted by a light source 1 is reflected by the mirror 6g to impinge upon a position detector 7, of which the output signal corresponding to the impingement location of the point of light, is evaluated in an electronic evaluating circuit 8 as described above. The arrangement shown can be used to determine the deformation caused in the test sample 4d as well as the deformation velocity in test procedures occurring at a high velocity.

FIG. 6a is a front view and FIG. 6b is a top view of an arrangement for measuring deformations caused by a tensile load and/or torque load applied to a test sample 4e. Two light sources 1a and 1b each emitting a sheet-like light beam 2c and 2d respectively are used in this embodiment. Each incident light beam 2c and 2d has a line cross-section. The light sources 1a and 1b may actually form a single light source generating incident light beam of sufficient width to simultaneously illuminate both band-shaped narrow mirrors 6h and 6i. The two narrow band-shaped mirrors 6h and 6i are arranged on the surface of a test sample 4e which is, for example, a flat test sample. The spacing 16 between the mirrors 6h and 6i represents the measurement baseline in a manner similar to the above described embodiments. The intersection between the narrow mirrors and the sheet-like incident light beam provides reflected light beams 2e and 2f having a well defined point cross-section. The incident light beams are so directed that the line-shaped cross-section of the incident light beam intersects each narrow band-shaped mirror essentially at a right angle RA. The width of each line-shaped light beam is chosen or adjusted so that it is at least as large as the expected measurement displacement required for the test sample 4e. Two light sources may each emit a single incident light beam for impinging on the respective mirror, but the beam widths must be sufficient to keep the narrow mirror within the beam for any expected displacement. Where only one wide beam is used, it must be wider than the spacing 16 plus any expected displacement.

The line cross-section light beam or beams 2e, 2f are reflected by each mirror 6h, 6i as an essentially point cross-section light beam 2e, 2f which impinges upon a respective position detector 7a, 7b cooperatively arranged for each mirror. The output signal of each detector is evaluated in an electronic evaluating circuit 8a, 8b. The impingement location of the light beam and the corresponding measurement of the deformation of the test sample is performed as described above.

It is advantageous to use digitally operating position detectors in the described arrangement because effects of stray and scattered light may simply be suppressed by using electronic means for such suppression in these detectors.

FIG. 6a illustrates how the embodiment of FIGS. 6a and 6b is capable of measuring distortions caused by tensile forces and compressive forces. These tensile and compressive forces change the spacing 16 between the band-shaped narrow mirrors 6h and 6i. The change in the spacing 16 is a measure of the distortion caused by tensile or compression loads as described above.

The embodiment of FIGS. 6a and 6b, however, is also capable of measuring distortions caused by torque loads as will now be described with reference to FIG. 6c showing a view similar to FIG. 6b using a flat test sample 4e'. The test sample 4e' is shown in two positions P1 and P2 and carries a narrow ribbon or band mirror 6h as in FIGS. 6a and 6b. The sample 4e' is distorted from the position P1' into the position P2' by a torque moment T. In the undistorted position P1' the light beam 2c is reflected as the reflected light beam 2e which impinges on the sensor 7a at point P1. The incident angle α1 is the same as the reflection angle α1. Due to the application of the testing torque moment T the test sample 4e' is twisted into the position P2', whereby the impingement point of the reflected beam 2e' on the sensor 7a travels from P1 to P2. The distance D travelled by the impingement point is sensed by the sensor 7a and evaluated by the circuit 8a shown in FIGS. 6a and 6b. This distance is a direct measure of the torque caused distortion.

The angle α2 is equal to the angle α2 but the measuring depends on the travel distance D and not on any changes in the angle of incidence nor in the reflection angle.

As just described for the light source 1a with its sensor 7a, the light source 1b with its sensor 7b can also sense a torque caused distortion and it is even possible to compare any differences that might be present between the distances D measured by the two pairs of light sources 1a, 1b and sensors 7a, 7b.

Although the invention has been described with reference to specific example embodiments, it will be appreciated that it is intended to cover all modifications and equivalents within the scope of the appended claims.

What we claim is:

1. A method for measuring deformations caused by at least one of a tensile force and a torque moment applied as a testing load to a test sample in a testing machine, comprising:
   (a) producing two sheet-like incident light beams;
   (b) directing both said sheet-like incident light beams at respective narrow band-shaped mirrors directly attached to said test sample for following a movement of said test sample in response to the application of said testing load to said test sample;
   (c) reflecting each of said sheet-like incident light beams by the respective band-shaped mirror to form two reflected light beams each having substantially a point cross-section;
   (d) receiving each of said reflected light beams on a respective position detector whereby said reflected light beams form an impingement location on each of said position detectors;
   (e) generating an output signal in each of said position detectors dependent on said impingement location to provide two output signals; and
   (f) evaluating said two output signals in an evaluating circuit to determine a movement of said impingement locations in response to an application of said testing load to said test sample, said movement representing a measure of said deformation.

2. The method of claim 1, wherein at least one of said reflected light beam is a collimated point cross-section light beams.

3. An apparatus for measuring deformations caused by at least one of a tensile force and a torque moment applied as a testing load to a test sample in a testing machine, comprising light source means for emitting sheet-like incident light beams, two narrow band-shaped reflecting mirrors directly attached to said test sample for following a movement of said test sample, said narrow band-shaped mirrors reflecting said sheet-like incident light beams to form two reflected light beams each having substantially a point cross-section, position detector means for receiving said reflected light beams and generating two output signals representing a movement of at least one impingement location in response to an application of said testing load to said test sample, and electronic evaluating circuit means connected to an output of said position detector means for evaluating said output signals to determine a deformation corresponding to said movement of said impingement location of said reflected light beams on said position detector means.

4. The apparatus of claim 3, wherein said light source means comprises a laser light source.

5. The apparatus of claim 3, wherein said position detector means comprise two position detectors and said electronic evaluating circuit means comprise evaluating circuit means for evaluating both output signals generated by said two position detectors.

6. The apparatus of claim 3, wherein said position detector means comprises a one-axis linear position detector.

7. The apparatus of claim 3, wherein said position detector means comprises a two-axes planar position detector.

8. The apparatus of claim 3, wherein said position detector means operates in an analog manner.

9. The apparatus of claim 3, wherein said position detector means operates in a digital manner.

* * * * *